United States Patent
Olsen et al.

(10) Patent No.: US 8,907,138 B1
(45) Date of Patent: Dec. 9, 2014

(54) USE OF A TREATED, PROMOTED ION EXCHANGE RESIN CATALYST

(71) Applicant: Rohm and Haas Company, Philadelphia, PA (US)

(72) Inventors: Robert James Olsen, Lansdale, PA (US); Gregory C. Pierce, Maple Glen, PA (US); Alfred K. Schultz, Maple Glen, PA (US); Klaus-Dieter Topp, Kromberg (DE)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/368,991

(22) PCT Filed: Dec. 14, 2012

(86) PCT No.: PCT/US2012/069695
§ 371 (c)(1),
(2), (4) Date: Jun. 26, 2014

(87) PCT Pub. No.: WO2013/101502
PCT Pub. Date: Jul. 4, 2013

Related U.S. Application Data

(60) Provisional application No. 61/581,067, filed on Dec. 28, 2011.

(51) Int. Cl.
*C07C 39/12* (2006.01)
*C07C 37/20* (2006.01)
*B01J 31/08* (2006.01)

(52) U.S. Cl.
CPC ............ *C07C 37/20* (2013.01); *B01J 31/08* (2013.01); *B01J 2231/40* (2013.01)
USPC .......................................... 568/729

(58) Field of Classification Search
USPC .......................................... 568/729
See application file for complete search history.

(56) References Cited

U.S. PATENT DOCUMENTS

| | | | |
|---|---|---|---|
| 4,400,555 A | 8/1983 | Mendiratta | |
| 4,973,607 A | 11/1990 | Stahlbush et al. | |
| 6,307,111 B1 | 10/2001 | Fenhoff et al. | |
| 6,465,697 B1 | 10/2002 | Palmer et al. | |
| 6,703,530 B2 | 3/2004 | Kissinger et al. | |
| 6,737,551 B2 | 5/2004 | Saruwatari | |
| 7,923,586 B2 | 4/2011 | Stahlbush et al. | |
| 2008/0319237 A1 | 12/2008 | Stahlbush et al. | |
| 2009/0156798 A1 | 6/2009 | Vanhoorne et al. | |
| 2010/0324341 A1 | 12/2010 | Terajima | |

OTHER PUBLICATIONS

Chiellini, Emo., et al, "Modified Ion-Exchange Sulfonic Resins: Thermostability and Catalytic Activity in Bisphenol A Synthesis", Chimica E L'Industria, Societa Chimica Italiano, Milano, IT, vol. 72, No. 12, pp. 991-996. Jan. 1, 1990. XP001526438.

*Primary Examiner* — Jafar Parsa
(74) *Attorney, Agent, or Firm* — Tifani Edwards

(57) ABSTRACT

The present invention relates to the use of an antioxidant treated promoted strong acid ion exchange resin as an acid catalyst.

7 Claims, No Drawings

USE OF A TREATED, PROMOTED ION EXCHANGE RESIN CATALYST

The present invention relates to the use of an antioxidant treated promoted strong acid ion exchange resin as an acid catalyst.

Polymeric promoted ion exchange resins, such as sulfonated styrene-divinylbenzene types of strong acid ion exchange resins are used as catalysts in the production of various organic chemicals including for example bisphenol-A and alkyl phenol. These catalysts are susceptible to oxidation during manufacture, storage, handling, processing, washing, and drying prior to use. Oxidative degradation leads to the release of low and medium molecular weight acidic material from the polymeric resins, such as low molecular weight organic sulfonates, sulfonated oligomers and sulfonated polystyrene polymers. Release of these acidic components into, for example, a bisphenol production process can lead to the generation of undesired impurities and color bodies, resulting in the production of off-spec product.

There is a need to protect ion exchange resins from oxidative degradation prior to and during storage; prior to and during washing; prior to and during drying; and prior to use of the ion exchange resin in a chemical production process.

U.S. Pat. No. 7,923,586 discloses the use of antioxidants to protect ion exchange resins from oxidative degradation. The patent describes that antioxidants are preferably added to the ion exchange resins at the time of manufacture. Although U.S. Pat. No. 7,923,586 discloses the use of antioxidants to protect ion exchange resins being manufactured from oxidative degradation, it does not disclose a process for decreasing the oxidative degradation of promoted ion exchange resins and thereby increasing the cleanliness of ion exchange resins already manufactured further comprising a promoter.

It is, therefore, desired to provide a process for producing dihydric phenol 2,2bis(4'-hydroxyphenyl) propane ("BPA") using a stabilized, promoted ion-exchange resin catalyst to prevent degradation of the resin prior to its use as a catalyst.

The present invention provides a process for producing dihydric phenol 2,2bis(4'-hydroxyphenyl) propane comprising condensing phenol with acetone in the presence of an acid catalyst to produce dihydric phenol 2,2bis(4'-hydroxyphenyl) propane;
wherein the acid catalyst is a promoted ion exchange resin catalyst contacted with an antioxidant to produce a treated promoted ion exchange resin catalyst.

For the purposes of describing the present invention, the "stability" of the resin refers to the resin's ability to withstand decomposition during storage, handling, processing, and drying. Decomposition is primarily caused by oxidation and can result in unwanted color throw, leachables and elevated total organic carbon (TOC) levels which can in turn affect the resin's performance and perceived quality. This unwanted color throw, leachables and elevated total organic carbon (TOC) levels contributes to a resin's cleanliness. A stabilized resin resists oxidation upon storage, handling, processing, and drying. Improving the stability of the resin enhances the resins ability to resist oxidative decomposition after long periods of storage, handling, processing, and drying eliminating the color throw, leachables and elevated TOC levels when such resin is brought into service. Such resins are said to be "cleaner resins"

Oxidative degradation can be observed as a progressive discoloration of a promoted ion exchange resin sample when stored without special precautions to prevent oxygen contact. Immersion of such a sample in water would result in a discoloration of the water, and a noticeable increase in the acidity and the TOC content of the water. An ion exchange resin that resists oxidative degradation is said to have good shelf life, and would not discolor significantly on storage, or cause a large increase in water color, acidity or TOC content when placed in water. Typical unstabilized ion exchange resins do not have good shelf life, and begin to discolor after storage of one month or less. A stabilized catalyst of the present invention, on the other hand, will have a shelf life of generally three months or more, preferably six months or more, and most preferably greater than one year.

The present invention prevents the degradation of a promoted ion exchange resin by treating the promoted ion exchange resin with an antioxidant.

As used herein the terms ion exchange resin, ion exchange resin catalyst, resin, ion exchange resin, ion exchange resin catalyst, catalyst, resin catalyst, and ion exchange resin are used interchangeably.

As used herein by promoted ion exchange resin is meant an ion exchange resin comprising a promoter. Suitable promoters of the present invention include but are not limited thiol promoters or other nucleophilic materials capable of increasing the reaction rate of the condensation reaction.

The term "thiol promoter" as used herein refers to a molecule incorporating a thiol (SH) group. The thiol promoter acts to improve the rate and selectivity of bisphenol formation when a hydroxyaromatic compound is condensed with an aldehyde or ketone in the presence of an acidic catalyst relative to the same reaction carried out in the absence of the thiol promoter.

Thiol promoters which may be employed include aliphatic, cylcoaliphatic and aromatic thiols which may be substituted by a basic group such as an amine or an acidic group such as a carboxylic acid. The thiol promoter may be used as a "bulk" promoter, that is a thiol promoter which is not adapted for attachment to the amine modified acidic resin, or an "attached" promoter. Where the thiol promoter contains a basic functional group such as an amine said thiol promoter may be attached to amine modified acidic resin catalyst and is referred to as an "attached" promoter. Functional groups present in the thiol promoter, other than amino groups, which facilitate the attachment of the thiol promoter to the amine modified acidic resin catalyst include amido, imido and carbamyl groups as are found in amides, imides and carbamates, respectively.

Bulk thiol promoters include cylcoaliphatic thiols such as cyclohexanethiol and cyclopentanethiol, aromatic thiols such as thiophenol and benzylthiol, and aliphatic thiols such as butanethiol, hexanethiol, octadecanethiol and 3-mercaptopropionic acid.

Attached thiol promoters include 2-mercaptomethylpyridine, cysteamine, and 4-aminobutanethiol immobilized in an amine modified acidic resin catalyst, for example a sulfonated polystyrene in which 10 to 30 percent, more preferred 20 to 25 percent of the sulfonic acid groups have been neutralized with the promotor.

The antioxidant and the steps necessary to apply the antioxidant to the promoted ion exchange resin are described below. The antioxidant is preferably added to the promoted ion exchange resin. The antioxidant should sequentially follow the addition of the promoter when producing a treated promoted ion exchange resin catalyst of the present invention The promoted ion exchange resin used in the present invention includes, for example, an ion exchange resin comprising a promoter. Ion exchange resins and processes for preparing ion exchange resins are well known in the art, as exemplified in Helfferich, *Ion Exchange*, McGraw-Hill Book Co., Inc., pp. 26-47 (1962). Advantageously, the resins are prepared by first copolymerizing one or more monovinyl monomers and one or more polyvinyl monomers to prepare a crosslinked copolymer matrix, and then functionalizing the copolymer matrix with groups which can exchange cations. Preferred monovinyl monomers include styrene and its derivatives, acrylic or methacrylic acid, esters of acrylic or methacrylic acid and mixtures thereof. More preferred monovinyl monomers are the monovinyl aromatic monomers, styrene being the most preferred. Preferred polyvinyl monomers include divinylbenzene (DVB)trivinylbenzene, and diacrylates or dimethacrylates. More preferred polyvinyl monomers are divinyl monomers, especially divinyl aromatic monomers. The most preferred polyvinyl monomer is DVB. A small amount of a third monomer may be added. Such monomers include for example polyacrylonitrile and ethylene glycol dimethacrylate. Amounts of such monomer may be, for example, less than 10 wt percent, preferably less than 5 wt percent, and more preferably less than 3 wt percent. The copolymer matrix is advantageously functionalized with sulfonic, phosphinic, phosphonic, arsenic, or carboxylic acid groups, or phenolic groups. The copolymer matrix is preferably functionalized with sulfonic acid groups.

Ion exchange resins useful in the present invention include for example styrene-divinylbenzene types of strong acid ion exchange resins such as DOWEX 50WX4, DOWEX 50WX2, DOWEX M-31, DOWEX MONOSPHERE M-31, DOWEX DR-2030 and DOWEX MONOSPHERE DR-2030 catalysts commercially available from The Dow Chemical Company.

Other examples of commercially available ion exchange resins useful in the present invention include Diaion SK104, Diaion SK1B, Diaion PK208, Diaion PK212 and Diaion PK216 manufactured by Mitsubishi Chemical Industries, Limited; AMBERLYST™-15, AMBERLYST™-35, AMBERLYST™-121, AMBERLYST™-232 and AMBERLYST™-131 manufactured by The Dow Chemical Company; T-38, T-66 and T-3825 manufactured by Thermax; Lewatit K1131, Lewatit K1221, Lewatit K1261 and Lewatit SC 104 manufactured by Lanxess; Indion 180 and Indion 225 manufactured by Ion Exchange India Limited; and Purolite CT-175, Purolite CT-222 and Purolite CT-122 manufactured by Purolite.

The sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. The sulfonated styrene-divinyl benzene copolymer copolymer being preferred. These resins can be used in gel, porous, or seeded forms. These resins can have narrow or broad particle size distributions. These resins can also be sulfone cross-linked, shell functionalized and or contain greater than one sulfonic acid group per benzene ring. And these resins can be used singly or in combinations of two or more.

Antioxidants that may be used in the present invention include soluble antioxidants and bound antioxidants. Soluble antioxidants can be applied to the promoted ion exchange resin by dissolving them in water, then mixing the water dissolved antioxidant with the promoted ion exchange resin. When the excess liquid is drained from the resin, a portion of the antioxidant would be retained in the water absorbed by the promoted ion exchange resin, if the promoted ion exchange resin is left in a "water wet" condition. In some cases, if desired, the soluble antioxidants can be removed from the promoted ion exchange resin prior to use; and in such cases the antioxidant may be removed from the promoted ion exchange resin prior to use by washing.

Bound antioxidants contain functionalities that cause the antioxidants to become bound to the sulfonic acid groups of the ion exchange resin. For example, 2,6-di-t-butyl-α-dimethylamino-p-cresol contains an amine group, a weak base, which binds strongly to the sulfonic acid groups of the ion exchange resin, and can only be rinsed off by using strong acids or by neutralizing the strong acid groups (neutralization would render the ion exchange resin unusable as a strong acid catalyst).

The antioxidant useful in the present invention are substances which retard deterioration of the ion exchange resin by oxidation over time and may include for example those described in U.S. Pat. No. 4,973,607. In addition the antioxidants used in the present invention may include those described in Dexter et al., *Encyclopedia of Polymer Science and Technology*, Copyright® 2002 by John Wiley & Sons, Inc.; Thomas et al., *Kirk-Othmer Encyclopedia of Chemical Technology*, Copyright© 2002 by John Wiley & Sons; Ash, Michael and Irene, *The Index of Antioxidants and Antiozonants*, Copyright 1997 by Gower; Denisov, E. T., *Handbook of Antioxidants*, Copyright 1995 by CRC Press; and *Index of Commercial Antioxidants and Antiozonants*, Copyright 1983 by Goodyear Chemicals; all of which are incorporated here by reference.

Antioxidants which may be used in the present invention include for example, monocyclic of polycyclic phenols, amines, diamines, hydroxylamines, thioesters, phosphites, quinolines, benzofuranones, or mixtures thereof. The antioxidant should preferably be unreactive in the chemical process for which the treated promoted ion exchange resin is intended, especially if a bound or copolymerized type of antioxidant is used. Other possible types of antioxidants that may be used in the present invention are described in U.S. Pat. No. 4,973,607.

Other examples of antioxidants useful in the practice of the present invention may include various chemical preservatives that are substances generally recognized as safe (GRAS) based upon the Code of Federal Regulations, for Food and Drugs, 21CFR182.1 Subpart D-Chemical Preservatives, reference 21CFR Parts 170-199, Apr. 1, 2001 revision. The preferred chemical preservatives for ion exchange resin are used to improve storage and to control color throw and TOC for long term storage. The additive to a typical strong acid ion exchange resin stabilizes said resin to reduce both visual and extractive color throw and to retard the development of TOC leachables. The antioxidants or preservatives are either GRAS or have been tested and approved for using in indirect food contacting applications. Examples of GRAS chemical preservatives can be found in Table I as listed in the Code of Federal Regulations 21, Part 182.1 Subpart D or as commercially tested and approved for indirect food contacting. They include for example, ascorbic acid, erythorbic acid, sorbic acid, thiodipropionic acid, calcium sorbate, dilauryl thiodipropionate, potassium metabisulfite, potassium sorbate, sodium ascorbate, sodium bisulfate, sodium metabisulfite, sodium sorbate, sodium sulfite, sulfur dioxide, tocopherols The promoted ion exchange resin should preferably contain enough antioxidant to effectively prevent oxidation of the resin prior to use. If a bound antioxidant is used, the promoted ion exchange resin should not contain so much antioxidant that the functionality of the acid resin is impaired. A permissible range might include an antioxidant content of from 0.001 to 10 percent of the promoted ion exchange resin by weight. A preferable range of antioxidant content may be from 0.01 to 2.0 percent by weight.

Various methods may be used to apply the antioxidant to the promoted ion exchange resin. For example, in one embodiment, the antioxidant may be applied to the promoted ion exchange resin by first preparing a solution of the antioxidant in water, and then mixing the aqueous antioxidant solution with the promoted ion exchange resin until at least a portion of the antioxidant present in the solution is adsorbed by the promoted ion exchange resin. The excess solution is then drained from the treated promoted ion exchange resin.

The aqueous antioxidant solution may contain other components that are either optional or necessary to form the solution. For example, the antioxidant 2,6-di-t-butyl-α-dimethylamino-p-cresol is sparingly soluble in water, and therefore an acid such as hydrochloric acid or sulfuric acid is preferably used to form an amine salt so that the antioxidant will become soluble.

The treated promoted ion exchange resin may be rinsed after the antioxidant solution is applied to remove the unabsorbed elements of the antioxidant from the resin. This rinsing step is particularly desirable if a bound antioxidant, such as 2,6-di-t-butyl-α-dimethylamino-p-cresol, is used; or if the antioxidant solution also contains other components that might cause problems in the subsequent use of the treated promoted ion exchange resin. For example, when treating a promoted ion exchange resin with a solution containing the hydrochloric acid salt of 2,6-di-t-butyl-α-dimethylamino-p-cresol, hydrochloric acid may be released. Thus, it may be preferable to rinse the hydrochloric acid from the stabilized promoted ion exchange resin after applying the hydrochloric acid salt of 2,6-di-t-butyl-α-dimethylamino-p-cresol to the promoted ion exchange resin.

Any combination of the foregoing treated promoted ion exchange resins of the present invention may be used in various chemical production processes where a catalyst is used and wherein there is a need to prevent catalyst oxidation regardless of the final end use. Such processes can include, for example, condensation reactions of phenols and ketones; phenol/acetone production; phenol or cresol alkylation. The antioxidants of the present invention are useful in processes wherein color and acid throw may be a problem and offer the potential to make cleaner, lower color solvents and the reduction of acid release which finally lead to higher product qualities.

The stabilized treated promoted ion exchange resin is preferably used in a process for producing the dihydric phenol 2,2bis(4'-hydroxyphenyl) propane (commonly referred to as "bisphenol A") which is commercially prepared by condensing phenol with acetone in the presence of an acid catalyst. Typically the phenol to acetone ration is 2:1 moles. In this reaction a mole of water is coproduced. The bisphenol A process is a well-known process and is described, for example in U.S. Pat. Nos. 4,400,555; 6,703,530; 6,307,111; 6,465,697; and 6,737,551.

The strong acid treated promoted ion exchange resins of the present invention generally show both a low color throw and a low TOC leachables after treatment with the antioxidant described above. Such benefits are shown after the resin is stored, for example, for up to 6 months with no significant increase in color throw and TOC leachables.

The following examples are included herein to illustrate the present invention; and are not to limit the scope of the present invention

EXAMPLES

Preparation of Resin for Testing

To establish a clean starting baseline, all the catalyst resins are given the same conditioning procedure in order to remove any residual acid from the plant process. A clean glass quart jar is filled with 350 mLs of fresh ion exchange resin and batch washed three times with 500 mLs of DI water. The resin is then charged to a 1" diameter jacketed glass column fitted with an FMI pump and a heating bath. The column is heated and maintained at 60° C. by the heating bath. The catalyst resin is backwashed by pumping 4 L of DI water through the column at 15 mL/min. After 4 liters of DI water has passed through the column the resin is transferred to a clean glass quart jar and batch washed again three times, but now with MilliQ $H_2O$. After the last batch wash the resin is siphoned dry using house vacuum for 60 seconds. The freshly cleaned resin is now ready for testing.

Addition of Promoter:

To a clean 1 L round-bottomed flask equipped with a Teflon stifling paddle is transferred 150 g of conditioned resin along with enough DI water for fluid stirring. The promoter solution is prepared by adding 1.50 g of Cysteamine-95 to 13.5 g of DI water. The mixture is stirred vigorously until dissolved and then transferred to an addition funnel. The promoter solution is charged to the catalyst resin drop wise over 60 minutes with stirring at RT. Following the addition of the promoter solution the addition funnel is rinsed with DI water into the round-bottomed flask. The catalyst resin is stifled for another 30 minutes following the end of the promoter addition. After 30 minutes the resin is washed 3 times (batchwise) with 500 mLs DI water to remove any residual promoter solution and the sample is then transferred to a clean quart jar. The loaded resin is again batch washed 3 times with 500 mls MilliQ water to remove any effect of the standard DI water. A 50 g sample of the treated resin is then transferred to a clean 8 oz jar and run through the stability test as described below.

Addition of Antioxidant:

To a clean 1 L round-bottomed flask equipped with a Teflon stifling paddle is transferred 150 g of conditioned resin along with enough tap DI water for fluid stifling. The antioxidant solution is prepared by adding 1.0 g of Ethanox-703 to 113.6 g of DI water along with 0.7 g of 96% $H_2SO_4$. The mixture is stirred vigorously until dissolved. To the conditioned resin in the round-bottomed flask is charged 11.53 g of the prepared Ethanox-703 solution. The loading of the antioxidant onto the resin takes place while the resin is stirring at RT for 30 minutes in the round-bottomed flask. After 30 minutes the resin is batched washed 3 times with 500 mLs DI water to remove any residual antioxidant solution and transferred to a clean quart jar. The loaded resin is again batch washed 3 times with 500 mLs MilliQ water to remove any effect of the standard DI water. A 50 g sample of the treated resin is then transferred to a clean 8 oz jar and run through the stability test as described below.

General Procedure for Stability Testing the Resin Samples:

To a clean 8 oz jar is transferred 50 g of conditioned resin. The correct amount of MilliQ water is charged to the resin (depending on the resin solids). The jar is sealed and placed on an auto shaker for 20 minutes at 140 rpm. After shaking, the resin and MillQ water are separated by using a clean glass funnel and Whatman filter paper. For samples being tested after aging, the resin is stored as 30 C for the requisite amount of time (see table below) followed by separating the resin and MillQ water by using a clean glass funnel and Whatman filter paper. The MilliQ water is filtered into a clean 4 oz jar and the catalyst resin is siphoned dry and stored in the 8 oz jar. The effluent MilliQ water is then tested for pH, and conductivity. These values are recorded in Table 1 below.

TABLE 1

Results of Stability Testing of Resins, Dependant on
Order of Addition of Promoter and Antioxidant.

| Resin | Treatment | Age (days) | pH | Conductivity (μS/cm) |
|---|---|---|---|---|
| AMBERLYST 31 | 1. Promoter 2. Antioxidant | 3 | 7.44 | 5 |
| AMBERLYST 31 | 1. Antioxidant 2. Promoter | 3 | 5.21 | 35 |
| AMBERLYST 121 | 1. Promoter 2. Antioxidant | 3 | 7.44 | 8 |
| AMBERLYST 121 | 1. Antioxidant 2. Promoter | 3 | 4.99 | 94 |
| AMBERLYST 131 | 1. Promoter 2. Antioxidant | 3 | 7.54 | 5 |
| AMBERLYST 131 | 1. Antioxidant 2. Promoter | 3 | 4.89 | 81 |
| DOWEX CM-4 | 1. Promoter 2. Antioxidant | 3 | 5.62 | 28 |
| DOWEX CM-4 | 1. Antioxidant 2. Promoter | 3 | 4.93 | 137 |
| DOWEX 50WX4 | 1. Promoter 2. Antioxidant | 3 | 6.61 | 9 |
| DOWEX 50WX4 | 1. Antioxidant 2. Promoter | 3 | 5.38 | 29 |

What is claimed is:

1. A process for producing dihydric phenol 2,2bis(4'-hydroxyphenyl) propane comprising condensing phenol with acetone in the presence of an acid catalyst to produce dihydric phenol 2,2bis(4'-hydroxyphenyl) propane;
wherein the acid catalyst is a promoted ion exchange resin catalyst contacted with an antioxidant to produce a treated promoted ion exchange resin catalyst.

2. The process of claim 1 wherein the ion exchange resin catalyst is a sulfonic acid-type cation-exchange resin catalyst.

3. The process of claim 2 wherein the cation-exchange resin catalyst is a sulfonated styrene-divinyl benzene copolymer.

4. The process of claim 1 wherein the antioxidant is a monocyclic or polycyclic phenol, an amine, a diamine, a thioester, a phosphate, a quinoline, or a mixture thereof.

5. The process of claim 1 wherein the antioxidant is 2,6-di-t-butyl-.alpha.-dimethylamino-p-cresol.

6. The process of claim 1 wherein the amount of antioxidant incorporated into the cation-exchange resin catalyst is from 0.001 to 10 percent by weight.

7. The process of claim 1 wherein the ratio of phenol to acetone is 2:1.

* * * * *